United States Patent
Xu et al.

(10) Patent No.: US 10,099,973 B2
(45) Date of Patent: Oct. 16, 2018

(54) METHOD FOR PREPARING P-XYLENE AND CO-PRODUCING PROPYLENE WITH HIGH SELECTIVITY

(71) Applicant: DALIAN INSTITUTE OF CHEMICAL PHYSICS, CHINESE ACADEMY OF SCIENCES, Dalian (CN)

(72) Inventors: Lei Xu, Dalian (CN); Zhongmin Liu, Dalian (CN); Xinzhi Zhang, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 0 days.

(21) Appl. No.: 15/315,603

(22) PCT Filed: Jun. 4, 2014

(86) PCT No.: PCT/CN2014/079144
§ 371 (c)(1),
(2) Date: Dec. 1, 2016

(87) PCT Pub. No.: WO2015/184600
PCT Pub. Date: Dec. 10, 2015

(65) Prior Publication Data
US 2017/0152197 A1    Jun. 1, 2017

(51) Int. Cl.
C07C 2/86       (2006.01)
B01J 29/40      (2006.01)
(Continued)

(52) U.S. Cl.
CPC ............... *C07C 2/864* (2013.01); *B01J 29/40* (2013.01); *C07C 2/865* (2013.01); *B01J 29/90* (2013.01);
(Continued)

(58) Field of Classification Search
None
See application file for complete search history.

(56) References Cited

U.S. PATENT DOCUMENTS 3,965,207 A    6/1976  Weinstein et al.
3,965,208 A    6/1976  Butter et al.
(Continued)

FOREIGN PATENT DOCUMENTS

CN       1830927 A          9/2006
CN     101239867 A    *    8/2008
(Continued)

OTHER PUBLICATIONS

Office Action issued by Intellectual Property Office of Singapore dated Jul. 13, 2017 for related Singapore Application No. 11201610150P.

*Primary Examiner* — In Suk C Bullock
*Assistant Examiner* — Ali Z Fadhel
(74) *Attorney, Agent, or Firm* — Enshan Hong; VLP Law Group LLP

(57) ABSTRACT

A method for preparing p-xylene and co-producing propylene with a high selectivity, comprising:
  a) bringing a raw material containing toluene and methanol and/or dimethyl ether into contact with a catalyst in a reaction system for reaction; returning an ethylene-enriched $C_2^-$ component discharged from the reaction system to the reaction system, and continuing the reaction with the raw material on the catalyst to produce propylene;
  b) separating a $C_6^+$ component discharged from the reaction system to obtain a product p-xylene; and
(Continued)

c) separating a $C_3$ component discharged from the reaction system to obtain a product propylene.

11 Claims, 4 Drawing Sheets

(51) Int. Cl.
  *B01J 38/12*  (2006.01)
  *B01J 29/90*  (2006.01)

(52) U.S. Cl.
  CPC ............ *B01J 38/12* (2013.01); *B01J 2229/32* (2013.01); *C07C 2529/40* (2013.01); *C07C 2529/80* (2013.01); *Y02P 20/52* (2015.11)

(56) References Cited

U.S. PATENT DOCUMENTS

| | | |
|---|---|---|
| 4,250,345 A | 2/1981 | Chu |
| 4,276,438 A | 6/1981 | Chu |
| 4,278,827 A | 7/1981 | Chu |
| 4,444,989 A | 4/1984 | Herkes |
| 4,491,678 A | 1/1985 | Oda |
| 4,670,616 A | 6/1987 | Simone |
| 5,034,362 A | 7/1991 | Chu |
| 5,563,310 A | 10/1996 | Chang et al. |
| 6,613,708 B1 | 9/2003 | Ou et al. |
| 2003/0004383 A1 | 1/2003 | Brown et al. |
| 2008/0161620 A1* | 7/2008 | Bozzano .................. C07C 1/24 585/449 |

FOREIGN PATENT DOCUMENTS

| | | |
|---|---|---|
| CN | 101239867 A | 8/2008 |
| CN | 101239867 A1 | 8/2008 |
| CN | 101417235 A | 4/2009 |
| CN | 101417236 A | 4/2009 |
| CN | 101456784 A | 6/2009 |
| CN | 101607858 A | 12/2009 |
| CN | 101456786 B | 12/2011 |
| CN | 101456785 B * | 5/2012 |
| CN | 101456785 B | 5/2012 |
| CN | 102464549 A | 5/2012 |
| CN | 102464550 B | 3/2014 |

* cited by examiner

METHOD FOR PREPARING P-XYLENE AND CO-PRODUCING PROPYLENE WITH HIGH SELECTIVITY

RELATED APPLICATIONS

This is a U.S. national stage of international application No. PCT/CN2014/079144 filed on Dec. 4, 2014.

TECHNICAL FIELD

This invention relates to a method for preparing p-xylene and co-producing propylene with a high selectivity from toluene and methanol and/or dimethyl ether, and pertains to the fields of chemistry and chemical industry.

BACKGROUND ART

P-xylene (hereinafter referred to as PX) and propylene are both important and valuable raw materials essential for chemical industry. At present, p-xylene is mainly obtained by an aromatic hydrocarbon combination apparatus. A reformate containing aromatic hydrocarbons is prepared by continuous reforming of naphtha, and a PX product is then maximally obtained via units of aromatic extraction, aromatic fractional distillation, disproportionation and transalkylation, xylene isomerization, and adsorptive separation, etc. Since the content of p-xylene among three isomers is thermodynamically controlled, and p-xylene comprises only about 23% in $C_8$ mixed aromatic hydrocarbons, the amount of recycling process is large, equipment is bulky, and the operational cost is high during the whole PX production process. Particularly, the differences between boiling points of three isomers of xylene are very small, high-purity p-xylene cannot be obtained with typical distillation techniques, and an expensive process for adsorptive separation has to be used. Propylene is mainly derived from byproducts in petroleum refineries and also from the production of ethylene by steam cracking of naphtha, or is produced by using propane as a raw material, which is prepared by processing of natural gas. p-Xylene is mainly used in the production of polyesters, and propylene is extremely useful in the preparation of polypropylene and acrylonitrile as well as 1,3-propylene glycol required in the production of polyesters. The rapid development of the global economy increasingly demands for p-xylene and propylene as essential chemical feedstock.

In recent years, there are a number of domestic and foreign patents that disclose new routes for the production of p-xylene, and among these, methylation of toluene may produce p-xylene with a high selectivity. U.S. Pat. No. 3,965,207 discloses that a ZSM-5 molecular sieve is used as a catalyst to perform methylation reaction of toluene, wherein the highest selectivity of p-xylene at a reaction temperature of 600° C. is about 90%; U.S. Pat. No. 3,965,208 uses a ZSM-5 molecular sieve modified with VA element as a catalyst, and the generation of m-xylene is inhibited and p-xylene and o-xylene are mainly generated, wherein the highest selectivity of p-xylene at a reaction temperature of 600° C. is about 90%; U.S. Pat. No. 4,250,345 uses a ZSM-5 molecular sieve modified with two elements phosphorus and magnesium as a catalyst, wherein the optimal selectivity of p-xylene at a reaction temperature of 450° C. is up to 98%; U.S. Pat. No. 4,670,616 prepares a catalyst by using a borosilicate molecular sieve and silicon oxide or aluminum oxide, wherein the selectivity of p-xylene is 50-60%; U.S. Pat. Nos. 4,276,438, and 4,278,827 use a molecular sieve having a special structure ($SiO_2$/$Al_2O_3 \geq 12$), which is modified with copper, silver, gold, germanium, tin, lead, etc., and a p-dialkylbenzene with a high selectivity can be obtained. U.S. Pat. No. 4,444,989 uses a crystalline pure silicon molecular sieve, which is modified with compounds of arsenic, phosphorus, magnesium, boron and, tellurium, and the selectivity of p-xylene is improved. U.S. Pat. No. 4,491,678 uses combined components of a crystalline borosilicate and elements of Group IIA and IIIA as well as silicon and phosphorus, and the selectivity of p-xylene may be greatly improved and the service life of the catalyst can be improved. U.S. Pat. No. 5,034,362 uses ZSM-5 and ZSM-11 wherein $SiO_2$/$Al_2O_3 \geq 12$ as catalysts and performs calcination under a condition of higher than 650° C., and the selectivity of p-dialkylbenzenes may be improved. U.S. Pat. No. 5,563,310 uses an acidic molecular sieve containing an element of Group IVB, which is modified with a metal of Group VIB, and the selectivity of p-dialkylbenzenes in alkylation reaction of toluene and methanol may be improved. U.S. Pat. No. 6,504,072 uses a mesoporous molecular sieve, preferably ZSM-5, which is treated in steam higher than 950° C. and then modified with phosphorus oxides, and proposes the influence of the diffusion effect of catalyst micropores on the selectivity of p-xylene. U.S. Pat. No. 6,613,708 uses an organic metal compound to modify a catalyst, and the selectivity of p-dialkylbenzenes may be greatly improved.

Chinese Patents ZL200610011662.4, ZL200710176269.5, ZL 200710176274.6, ZL 200710179408.X, ZL 200710179409.4, and ZL 200710179410.7 disclose a class of methods for preparing p-xylene and co-producing light olefins from toluene and methanol, indicating that ethylene and propylene may be co-produced with a high selectivity at the same time of preparing p-xylene with also a high selectivity, wherein the selectivity of p-xylene in xylene isomers is up to 99 wt % or more and the selectivities of ethylene and propylene in $C_1$-$C_5$ light hydrocarbons may be 90 wt % or more. However, the disadvantages of this method are that a cryogenic separation technique has to be used if a highly pure ethylene product is to be obtained, and that the investment and energy consumption are both high, which directly affects the economy of this process.

CN102464549 A discloses a method for producing propylene and p-xylene, comprising preparing propylene by the comproportionation of ethylene and C4 hydrocarbons, wherein the process for preparing propylene by the alkylation of ethylene and methanol/dimethyl ether is not involved. CN102464550 A discloses a method for co-production of light olefins and p-xylene, comprising preparing olefins by passing C4 and C5 hydrocarbons into a first reaction zone, which is a process of preparing olefins by cracking of $C_4$ or liquefied gas, wherein the process for preparing propylene by the alkylation of ethylene and methanol/dimethyl ether is not involved either.

SUMMARY OF THE INVENTION

An object of this invention is to provide a method for preparing p-xylene and co-producing propylene with a high selectivity from toluene and methanol and/or dimethyl ether.

To this end, this invention provides a method for preparing p-xylene and co-producing propylene with a high selectivity, comprising the steps of:

a) bringing a raw material containing toluene and methanol and/or dimethyl ether into contact with a catalyst in a reaction system for reaction, returning an ethylene-enriched $C_2^-$ component discharged from the reaction system to the reaction system, and continuing the reaction with the raw material on the catalyst to produce propylene;

b) separating a $C_6^+$ component discharged from the reaction system to obtain a product p-xylene; and c) separating a $C_3$ component discharged from the reaction system to obtain a product propylene.

Preferably, the catalyst is a modified zeolite molecular sieve catalyst, which is obtained from ZSM-5 and/or ZSM-11 zeolite molecular sieves by hydrothermal treatment and surface modification of a siloxanyl compound. More preferably, in the modified zeolite molecular sieve catalyst, the amount of Si loaded by siloxanyl compound modification is 1-10 wt % based on the total weight of the modified zeolite molecular sieve catalyst.

In one preferred embodiment, the reaction system comprises a first reaction zone and a second reaction zone, and the method comprises the steps of:

a) passing a raw material containing toluene and methanol and/or dimethyl ether through the first reaction zone to be in contact with a catalyst I for reaction, and then into the second reaction zone to be in contact with a catalyst II for reaction; returning an ethylene-enriched $C_2^-$ component discharged from the second reaction zone to the second reaction zone, and continuing reaction with methanol and/or dimethyl ether within the second reaction zone on the catalyst II to produce propylene;

b) further separating a $C_6^+$ component discharged from the second reaction zone to obtain a product p-xylene; and c) further separating a $C_3$ component discharged from the second reaction zone to obtain propylene.

In one preferred embodiment, the reaction system comprises a first reaction zone and a second reaction zone, and the method comprises the steps of:

a) passing a raw material containing toluene and methanol and/or dimethyl ether through the first reaction zone to be in contact with a catalyst I for reaction to obtain a resultant A, and then passing through the second reaction zone to be in contact with a catalyst II for reaction to obtain a resultant B; passing an ethylene-enriched $C_2^-$ component in the resultant A and the resultant B into the second reaction zone, and continuing reaction with methanol and/or dimethyl ether within the second reaction zone on the catalyst II to produce propylene;

b) further separating a $C_6^+$ component in the resultant A and the resultant B to obtain a product p-xylene; and c) further separating a $C_3$ component in the resultant A and the resultant B to obtain a product propylene.

In one preferred embodiment, the catalyst I and the catalyst II are the same or different modified zeolite molecular sieve catalyst(s).

In one preferred embodiment, the modified zeolite molecular sieve catalyst is obtained from ZSM-5 and/or ZSM-11 zeolite molecular sieves via hydrothermal treatment and modification of a siloxanyl compound.

In one preferred embodiment, in the modified zeolite molecular sieve catalyst, the amount of Si loaded by siloxanyl compound modification is 1-10 wt % based on the total weight of the modified zeolite molecular sieve catalyst.

In one preferred embodiment, the conditions for the hydrothermal treatment are treating under an atmosphere of saturated steam at 500-700° C. for 3-6 hours.

In one preferred embodiment, the siloxanyl compound used in the siloxanyl compound modification has a structural formula as shown by the following formula:

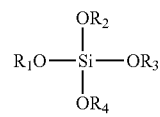

wherein $R_1$, $R_2$, $R_3$, and $R_4$ are each independently a $C_{1-10}$ alkyl group.

In one preferred embodiment, the siloxanyl compound is tetraethyl orthosilicate.

In one preferred embodiment, the reaction zone comprises a reactor or a plurality of reactors connected in series and/or in parallel; and preferably, the reactor is one or more selected from a fixed bed reactor, a fluidized bed reactor, and a moving bed reactor.

In one preferred embodiment, the first reaction zone and the second reaction zone are in the same reactor; and preferably, the reactor is one or more selected from a fixed bed reactor, a fluidized bed reactor, and a moving bed reactor.

In one preferred embodiment, the first reaction zone comprises a reactor or a plurality of reactors connected in series and/or in parallel; the second reaction zone comprises a reactor or a plurality of reactors connected in series and/or in parallel; and the first reaction zone and the second reaction zone are connected in series or in parallel; and preferably, the reactor is one or more optionally selected from a fixed bed reactor, a fluidized bed reactor, and a moving bed reactor.

The advantageous effects of this invention include, but are not limited to, the following aspects: this invention provides a new method for preparing p-xylene and co-producing propylene with a high selectivity via the reaction of toluene and methanol and/or dimethyl ether. In the method of this invention, a specific modified molecular sieve catalyst is used, an ethylene-enriched $C_2^-$ component in resultant products is returned to the reaction system and subjected to an alkylation reaction with methanol and/or dimethyl ether to further produce propylene, and p-xylene and propylene are finally obtained with a high selectivity. On one hand, high cost for separation of the ethylene product is avoided, and on the other hand, the production of propylene product with larger market demand may be further increased, such that the economy of this technique may be effectively improved.

DESCRIPTION OF EMBODIMENTS

Figure 1:
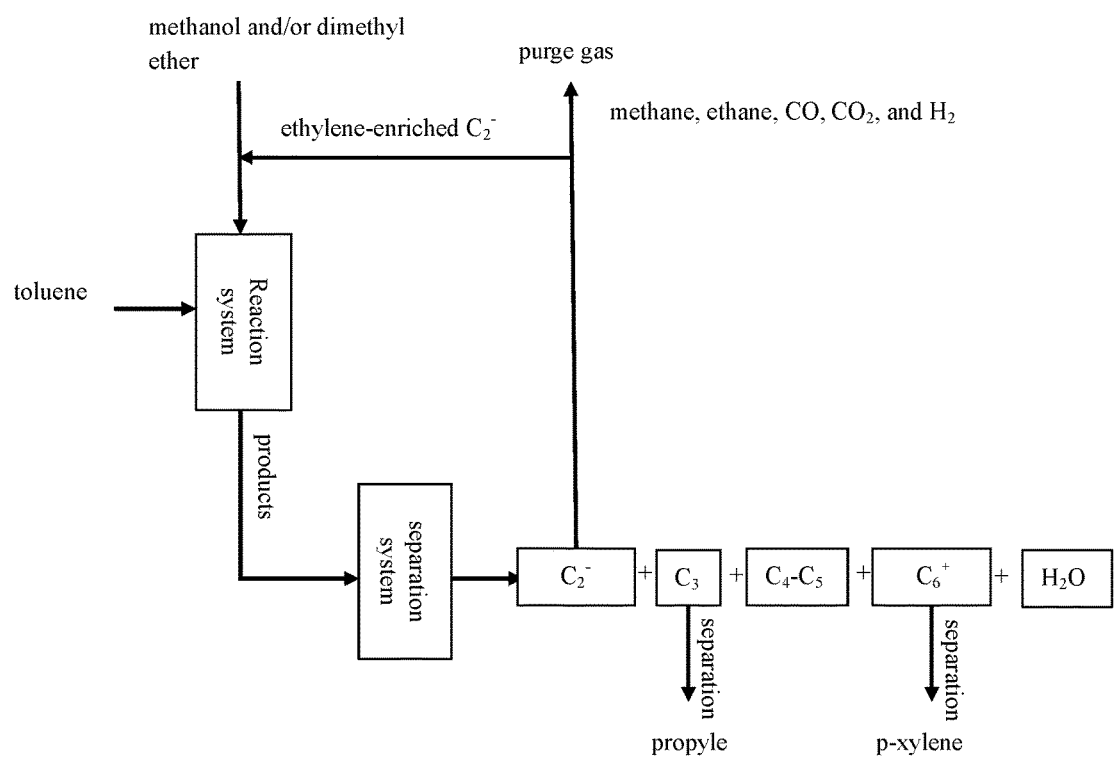
FIG. 1 is a flow chart of a method of an embodiment according to this invention.

In the method of this invention, two reaction processes, an alkylation reaction of toluene and methanol and/or dimethyl ether and an alkylation reaction of ethylene with methanol and/or dimethyl ether are coupled, meanwhile p-xylene and propylene are co-produced with a high selectivity. Specifically, a reaction process flow of the method of this invention is as shown in FIG. 1. Toluene and methanol and/or dimethyl ether as raw materials are brought into contact with a catalyst (the catalyst is present in a reactor) in a reaction system, and resultant products are passed into a separation system (for example, a fractionating tower, etc.) for separation; after separation by a separation system, a $C_6^+$ component, a $C_4$-$C_5$ component (hydrocarbons having carbon numbers of 4 and 5), a $C_3$ component, an ethylene-enriched $C_2^-$ component, and water ($H_2O$) are obtained, wherein, the ethylene-enriched $C_2^-$ component is returned to the reaction system, the $C_6^+$ component is subjected to further separation (for example, a rectification column, a crystallization separation system, etc.) to obtain p-xylene, the $C_3$ component is subjected to further separation (for example, a rectification column, etc.) to obtain propylene, and a small amount of the $C_4$-$C_5$ component and $H_2O$ are collected and used for other purposes, where the reaction system may be a separate reaction zone, or may be a combination of two or more reaction zones. A plurality of reaction zones may be in the same reactor, or may be in a plurality of reactors connected in series or in parallel. Preferably, the reactor is any one or more of a fixed bed, a fluidized bed, or a moving bed.

In this invention, the raw materials include toluene and methanol and/or dimethyl ether, indicating that the raw materials may be a mixture of toluene, methanol, and dimethyl ether, a mixture of toluene and methanol, or a mixture of toluene and dimethyl ether. Suitable kinds and compositional ratios of raw materials may be selected by the person skilled in the art according to requirements of actual production.

Figure 2:
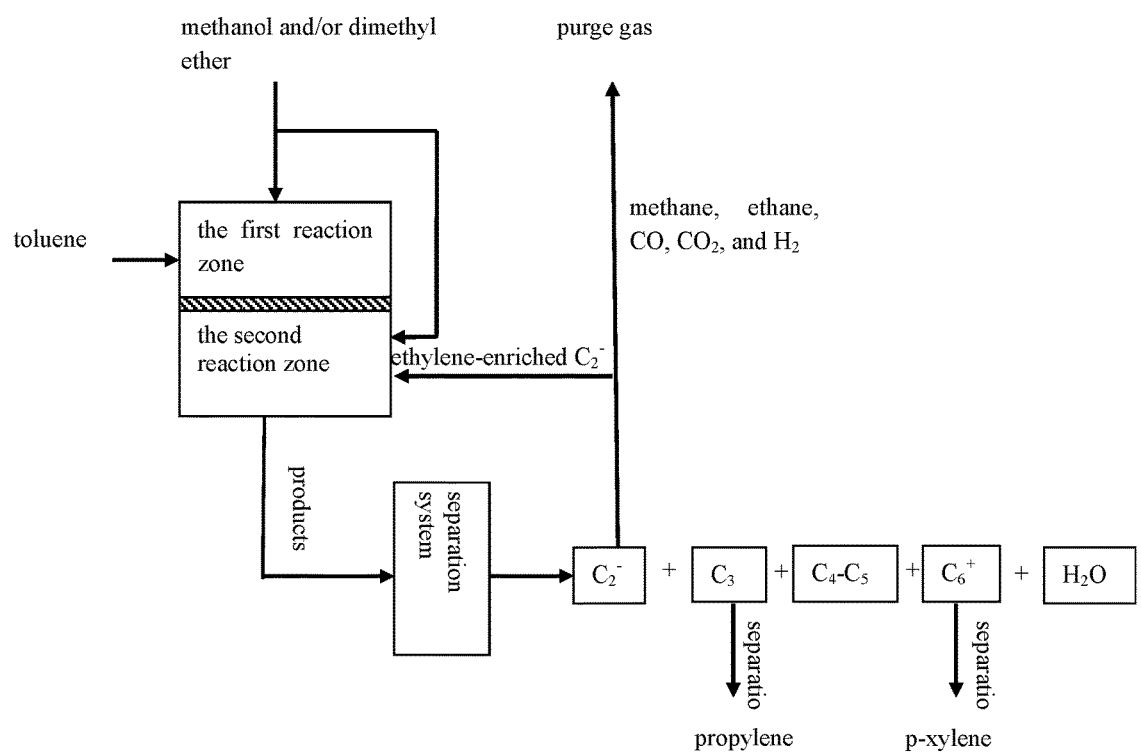
FIG. 2 is a flow chart of a method of another embodiment according to this invention.

In one preferred embodiment, a reaction process flow of a method according to this invention is as shown in FIG. 2. In FIG. 2, the reaction system is composed of one reactor having two reaction zones, wherein the main reaction in the first reaction zone is alkylation reaction of toluene and methanol and/or dimethyl ether, and the main reaction in the second reaction zone is alkylation reaction between ethylene (a byproduct of the first reaction zone) and methanol and/or dimethyl ether. Toluene and methanol and/or dimethyl ether as raw materials are passed through the first reaction zone to be in contact with a catalyst I therein for reaction, and then passed through the second reaction zone to be in contact with a catalyst II therein for reaction, and resultant products are passed into a separation system for separation; a $C_6^+$ component, a $C_4$-$C_5$ component, a $C_3$ component, a $C_2^-$ component, and $H_2O$ are obtained after separation by a separation system, wherein the ethylene-enriched $C_2^-$ component is returned to the second reaction zone and subjected to reaction with methanol and/or dimethyl ether that are passed into the second reaction zone in contact with the catalyst II therein; the $C_6^+$ component is subjected to further separation to obtain p-xylene, and the $C_3$ component is subjected to further separation to obtain propylene.

Figure 3:
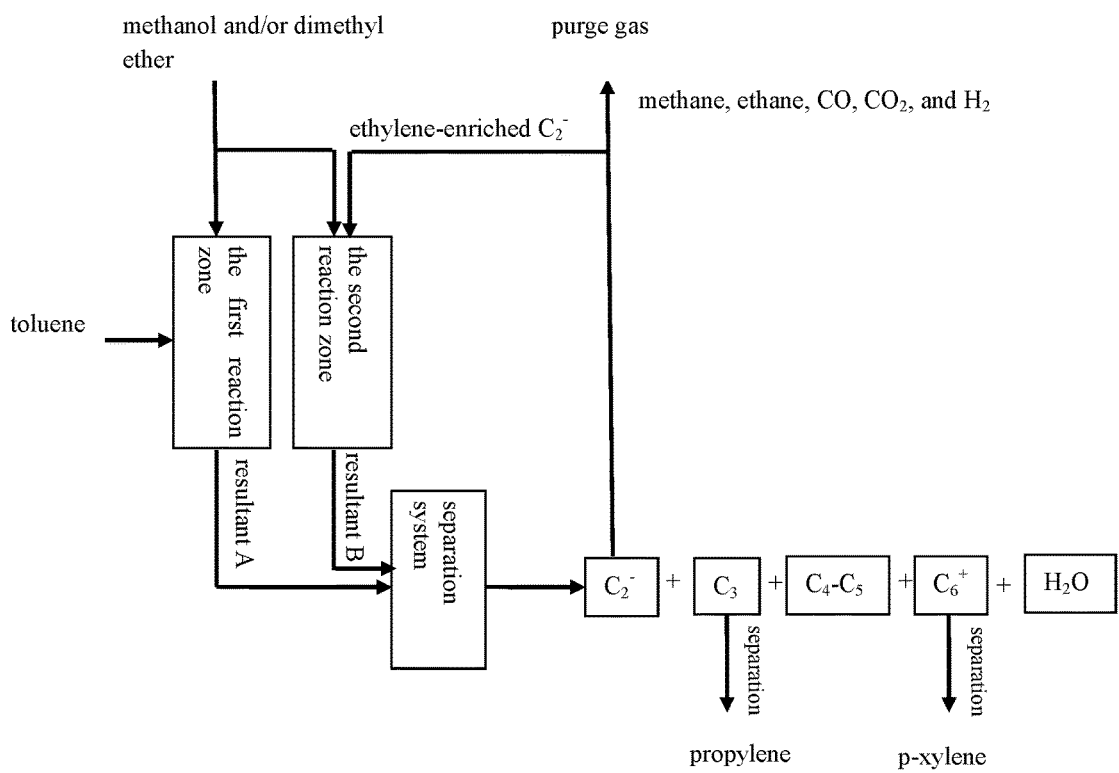
FIG. 3 is a flow chart of a method of another embodiment according to this invention.

In one preferred embodiment, a reaction process flow of a method according to this invention is as shown in FIG. 3. In FIG. 3, the reaction system is composed of two parallel reaction zones, wherein the main reaction in the first reaction zone is alkylation reaction of toluene and methanol and/or dimethyl ether, and the main reaction in the second reaction zone is alkylation reaction between ethylene (a byproduct of the first reaction zone) and methanol and/or dimethyl ether. Toluene and methanol and/or dimethyl ether are brought into contact with a catalyst I in a first reaction zone to generate a resultant A, and the resultant A is passed into a separation system for separation; an ethylene-enriched $C_2^-$ component from the separation system is returned to a second reaction zone and reacts with methanol and/or dimethyl ether as raw materials that are directly passed into the second reaction zone on a catalyst II therein to generate a resultant B, and the resultant B is passed into a separation system for separation together with the resultant A; after separation by the separation system, the ethylene-enriched $C_2^-$ component therein is returned to the second reaction zone, a $C_6^+$ component, which is obtained after the resultant A and the resultant B are separated by a separation system, is subjected to further separation to obtain p-xylene, and the $C_3$ component is subjected to further separation to obtain propylene.

Figure 4:
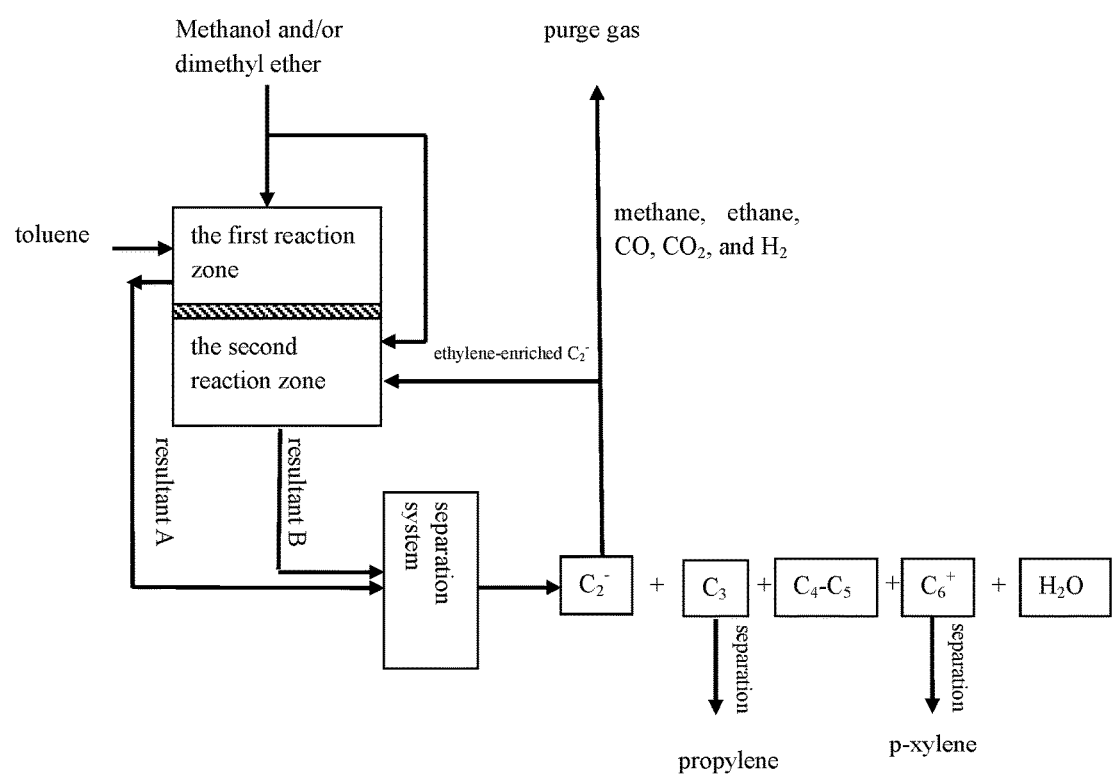
FIG. 4 is a flow chart of a method of another embodiment according to this invention.

In one preferred embodiment, a reaction process flow of a method according to this invention is as shown in FIG. 4. In FIG. 4, the reaction process is the same as the above process described for FIG. 3, except that the reaction system is composed of two reaction zones in the same reactor, and verbose words are omitted herein. This reaction system may be achieved by multi-sectional feeding.

In this invention, the catalyst used contains ZSM-5 and/or ZSM-11 zeolite molecular sieves, more preferably modified ZSM-5 and/or ZSM-11 zeolite molecular sieves obtained from ZSM-5 and/or ZSM-11 zeolite molecular sieves by hydrothermal treatment and modification of the surface acidity and the pore structure with a siloxanyl compound. Most preferably, after modification with a siloxanyl compound, the loading amount of Si is 1-10 wt % based on the total weight of this catalyst. When there are two reaction zones, the catalyst I and the catalyst II present therein respectively may be catalysts having the same or component(s). For example, in one preferred embodiment, the catalyst I and the catalyst II are the same kind of catalysts or the same catalyst.

In one preferred embodiment, the preparation process for the catalyst used in this invention is as follows.

(1) ZSM-5 and/or ZSM-11 zeolite molecular sieve raw powders are prepared into acidic zeolite molecular sieves by $NH_4^+$ ion exchange and calcination;

(2) the above acidic zeolite molecular sieves are subjected to hydrothermal treatment to obtain modified zeolite molecular sieves. Preferably, the condition of the hydrothermal treatment is treating under an atmosphere of saturated steam at 500-700° C. for 3-6 hours.

(3) the above modified zeolite molecular sieves are subjected to a surface modification by using a siloxanyl agent to further adjust the outer surface acidity and the pore structure of the molecular sieves so as to obtain modified zeolite molecular sieve catalysts.

Preferably, the siloxanyl compound used in this invention has a formula as shown by the following formula:

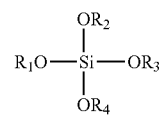

wherein $R_1$, $R_2$, $R_3$, $R_4$ are each independently a $C_{1-10}$ alkyl group, such as a methyl group, an ethyl group, a propyl group, a butyl group, a pentyl group, a hexyl group, a heptyl group, and a octyl group, as well as isomeric forms thereof.

Preferably, the siloxanyl compound used is tetraethyl orthosilicate.

Preferably, in either the first reaction zone or the second reaction zone in this invention, a fixed bed reaction process may be used, meanwhile a fluidized bed or moving bed reaction process in conjunction with a regenerator may be used. The first reaction zone and the second reaction zone may be respectively in one reactor or a plurality of reactors connected in series or in parallel, being the same or different, and are achieved by multi-sectional feeding.

In the method of this invention, the reaction temperature of alkylation of toluene and methanol and/or dimethyl ether, the reaction temperature of alkylation of ethylene and methanol and/or dimethyl ether are in the range 300-600° C. The reaction temperature of alkylation of toluene and methanol and/or dimethyl ether is preferably 400-500° C., and the preferred reaction temperature of alkylation of ethylene and methanol and/or dimethyl ether is 350-450° C. The mass hourly space velocity of alkylation reaction of toluene and methanol and/or dimethyl ether is 0.1-10 $h^{-1}$, and preferably 1-5 $h^{-1}$, in terms of toluene.

As for the method of this invention, in alkylation reaction of toluene and methanol and/or dimethyl ether, the feed molar ratio of toluene to methanol and/or dimethyl ether may be in a range of 0.1-10, preferably 0.2-5; and in alkylation reaction of ethylene and methanol and/or dimethyl ether, the molar ratio of ethylene to methanol and/or dimethyl ether may be in a range of 0.1-10, preferably 0.5-5.

Furthermore, in the method of this invention, the ratio of p-xylene to propylene in products can be controlled in a certain range by adjusting conditions such as the reaction temperature, the feed ratio of toluene to methanol and/or dimethyl ether, and the ratio of ethylene to methanol and/or dimethyl ether.

In this invention, the $C_2^-$ component refers to a component of which the molecular formula has a carbon atom number less than or equal to 2, and includes ethylene, ethane, methane, CO, $CO_2$, together with $H_2$, etc. The purge gas is mainly ethane, methane, CO, $CO_2$, together with $H_2$, etc.

In this invention, the $C_3$ component refers to a compound of which the molecular formula has a carbon atom number equal to 3, and includes propylene, propane, etc.

In this invention, the $C_4$-$C_5$ component refers to a component of which the molecular formula has a carbon atom number equal to 4 and 5, and includes isobutane, isobutene, butane, 1-butene, 2-butene, isopentane, neopentane, n-pentane, 1-pentene, 2-pentene, etc.

In this invention, the $C_6^+$ component refers to a component of which the molecular formula has a carbon atom number greater than or equal to 6, and includes p-xylene and other aromatic hydrocarbons and derivatives thereof, etc.

This present invention will be described in detail below by Examples, but this invention is not limited to these Examples.

The composition of products is analyzed online by a gas chromatograph, and the analysis conditions are:
Model: Varian CP3800
Column: CP Wax 52 CB capillary chromatographic column
Carrier gas: helium gas, 5 ml/min
Temperature of column box: 60-220° C., programmed temperature increasing at 15° C./min
Temperature of feed port: 260° C.
Detector: hydrogen flame ionization detector (FID)
Temperature of detector: 300° C.

Example 1

Preparation of Catalysts: Si-HZSM-5 Zeolite Molecular Sieve Catalyst and Si-HZSM-11 Zeolite Molecular Sieve Catalyst 500 g of ZSM-5 zeolite molecular sieve raw powder ($SiO_2$/$Al_2O_3$=68) (Catalyst Plant of Fushun Petrochemical Company) and 500 g of ZSM-11 zeolite molecular sieve raw powder ($SiO_2$/$Al_2O_3$=50) (Catalyst Plant of Nankai University) were calcined respectively at 550° C. to remove template agents, exchanged with 0.5 molar equivalents of an ammonium nitrate solution in a water bath at 80° C. for 4 times, dried at 120° C. in the air after exchange, and calcined at 550° C. for 4 hours so as to obtain a HZSM-5 zeolite molecular sieve and a HZSM-11 zeolite molecular sieve respectively.

The HZSM-5 zeolite molecular sieve and the HZSM-11 zeolite molecular sieve were modified by hydrothermal treatment respectively as follows: 100 g of each of the HZSM-5 zeolite molecular sieve and the HZSM-11 zeolite molecular sieve was placed in a quartz reactor respectively, water was introduced at a flow rate of 5 ml/min after the temperature was increased to 650° C., and a homothermal treatment was performed for 4 hours to obtain a hydrothermally modified HZSM-5 zeolite molecular sieve and a hydrothermally modified HZSM-11 zeolite molecular sieve. Surface modification was respectively performed on the hydrothermally modified HZSM-5 zeolite molecular sieve and HZSM-11 zeolite molecular sieve by using tetraethyl orthosilicate as a siloxane agent, and the steps were as follow: the hydrothermally modified HZSM-5 zeolite molecular sieve and HZSM-11 zeolite molecular sieve were respectively placed into 150 g of tetraethyl orthosilicate and soaked overnight, dried at 120° C. after liquid was decanted, and calcined in the air at 550° C. for 4 hours to obtain a modified Si-HZSM-5 zeolite molecular sieve catalyst and a hydrothermally modified Si-HZSM-11 zeolite molecular sieve catalyst respectively. They were named as catalysts TMPC-06 and TMPC-07.

Example 2

Preparation of Catalysts: A Mixed Catalyst of Si-HZSM-5 and Si-HZSM-11 Zeolite Molecular Sieves 200 g of ZSM-5 zeolite molecular sieve raw powder ($SiO_2$/$Al_2O_3$=61) (Fushun Catalyst Plant) and 300 g of ZSM-11 zeolite molecular sieve raw powder ($SiO_2$/$Al_2O_3$=50) were calcined at 550° C. to remove template agents, exchanged with 0.5 molar equivalents of an ammonium nitrate solution in a water bath at 80° C. for 4 times, dried at 120° C. in the air after exchange, and calcined at 550° C. for 4 hours so as to obtain a HZSM-5/HZSM-11 zeolite molecular sieve.

The HZSM-5/HZSM-11 zeolite molecular sieve was modified by hydrothermal treatment as follows: 100 g of the HZSM-5/HZSM-11 molecular sieve was placed in a quartz reactor, water was introduced at a flow rate of 5 ml/min after the temperature was increased to 650° C., and a homothermal treatment was performed for 4 hours to obtain a hydrothermally modified HZSM-5/HZSM-11 zeolite molecular sieve.

Surface modification was performed on the hydrothermally modified HZSM-5/HZSM-11 zeolite molecular sieve by using tetraethyl orthosilicate as a siloxane agent, and the steps were as follow: the hydrothermally modified HZSM-5/HZSM-11 zeolite molecular sieve was placed into 150 g of tetraethyl orthosilicate and soaked overnight, dried at 120° C. after liquid was decanted, and calcined in the air at 550° C. for 4 hours to obtain a modified Si-HZSM-5/HZSM-11 zeolite molecular sieve catalyst. It was named as catalyst TMPC-08.

Example 3

Preparation of p-Xylene and Co-Production of Propylene Via Reaction of Toluene with Methanol According to the reaction process flow shown in FIG. 2, catalyst samples of catalysts TMPC-06, TMPC-07, and TMPC-08 prepared in Examples 1 and 2 were subjected to tablet compression molding and 40-60 mesh target catalysts were obtained by cracking and sieving, each of the catalysts was charged to each of two reaction zones of a fixed bed reactor (10 g for each reaction zone). Conversion reaction of toluene and methanol was carried out in a first reaction zone, wherein the molar ratios of toluene/methanol can be seen in Table 1 below. Alkylation reaction of ethylene and methanol was carried out in a second reaction zone. When a reaction with a certain ratio therein was finished, nitrogen gas was introduced online for purging and then switched to air to regenerate the catalysts under a condition of 550° C. for 5 hours, where an ethylene-enriched $C_2^-$ component and methanol in the reaction product distribution of alkylation of toluene and methanol in the first reaction zone were passed together into the second reaction zone for reaction, wherein the molar ratio of ethylene/methanol was 1/1.

Reaction conditions: in the first reaction zone, the mass hourly space velocity of toluene was 2 $h^{-1}$ and the reaction temperature was 480° C.; in the second reaction zone, the reaction temperature was 420° C. The composition of mixed products in the reaction zones was analyzed online by using a gas chromatograph. The product distribution was as shown in Table 1 after resultant water was removed, and the product distribution was as shown in Table 2 after the $C_2^-$ component was further removed.

It can be seen from the data of Table 2 that on catalysts TMPC-06, TMPC-07, and TMPC-08, when feed molar ratios of toluene/methanol were 2/1, 1/1, and 1/2 respectively, the selectivities of propylene in total products were 26.19 wt %, 31.75 wt %, and 41.28 wt % respectively, and the selectivities of p-xylene were 62.38 wt %, 56.66 wt %, and 45.45 wt % respectively; and the overall selectivities of propylene and p-xylene were 88.57 wt %, 88.41 wt %, and 86.73 wt % respectively. The selectivities of p-xylene in xylene isomers were 98.34 wt %, 98.15 wt %, and 97.63 wt % respectively.

TABLE 1

|  | Catalyst | | |
| --- | --- | --- | --- |
|  | TMPC-06 | TMPC-07 | TMPC-08 |
| Feeding time (hour) | 1 | 1 | 1 |
| Toluene/methanol (molar ratio) in the first reaction zone | 2/1 | 1/1 | 1/2 |
| Ethylene/methanol (molar ratio) in the second reaction zone | 1/1 | 1/1 | 1/1 |
| Product distribution (wt %*) | | | |
| $CH_4$ | 0.91 | 1.09 | 1.38 |
| $C_2H_4$ | 11.51 | 13.80 | 19.01 |
| $C_2H_6$ | 0.29 | 0.21 | 0.24 |
| $C_3H_6$ | 22.86 | 26.96 | 32.76 |
| $C_3H_8$ | 0.52 | 0.55 | 0.58 |
| $C_4$ | 1.44 | 1.96 | 2.69 |
| $C_5$ | 0.57 | 0.71 | 0.89 |
| Benzene | 0.06 | 0.03 | 0.10 |
| Ethylbenzene | 0.21 | 0.15 | 0.19 |
| p-Xylene | 54.46 | 48.10 | 36.07 |
| m-Xylene | 0.34 | 0.25 | 0.32 |

TABLE 1-continued

|  | Catalyst | | |
| --- | --- | --- | --- |
|  | TMPC-06 | TMPC-07 | TMPC-08 |
| o-Xylene | 0.58 | 0.66 | 0.55 |
| $\geq C_9$ | 6.27 | 5.54 | 5.21 |
| Total | 100.00 | 100.00 | 100.00 |

*wt %, weight percentage composition of products, the same shall apply hereinafter.

TABLE 2

|  | Catalyst | | |
| --- | --- | --- | --- |
|  | TMPC-06 | TMPC-07 | TMPC-08 |
| Feeding time (hour) | 1 | 1 | 1 |
| Toluene/methanol (molar ratio) in the first reaction zone | 2/1 | 1/1 | 1/2 |
| Ethylene/methanol (molar ratio) in the second reaction zone | 1/1 | 1/1 | 1/1 |
| Product distribution (wt %) | | | |
| $C_3H_6$ | 26.19 | 31.75 | 41.28 |
| $C_3H_8$ | 0.59 | 0.65 | 0.74 |
| $C_4$ | 1.64 | 2.30 | 3.38 |
| $C_5$ | 0.65 | 0.83 | 1.12 |
| Benzene | 0.07 | 0.04 | 0.13 |
| Ethylbenzene | 0.24 | 0.18 | 0.24 |
| p-Xylene | 62.38 | 56.66 | 45.45 |
| m-Xylene | 0.39 | 0.30 | 0.41 |
| o-Xylene | 0.66 | 0.77 | 0.70 |
| $\geq C_9$ | 7.18 | 6.52 | 6.57 |
| Total | 100.00 | 100.00 | 100.00 |

Example 4

Preparation of p-Xylene and Co-Production of Propylene Via Reaction of Toluene with Methanol According to the reaction process flow shown in FIG. 3 or 4, a TMPC-06 catalyst prepared in Example 1 was subjected to tablet compression molding and a 40-60 mesh target catalyst sample was obtained by cracking and sieving, the catalyst was charged to each of two reaction zones of a fixed bed reactor (10 g for each reaction zone). Conversion reaction of toluene and methanol was carried out in a first reaction zone, wherein the molar ratios of toluene/methanol were 4/1, 2/1, 1/1, and 1/2 respectively (see Table 3 below). Alkylation reaction of ethylene and methanol was carried out in a second reaction zone, where an ethylene-enriched $C_2^-$ component and methanol in the reaction product distribution of alkylation of toluene and methanol in the first reaction zone were passed together into the second reaction zone for reaction, wherein the molar ratio of ethylene/methanol was 1/1.

Once a reaction with a certain ratio therein was completed, nitrogen gas was introduced to both the first reaction zone and the second reaction zone online for purging, and then switched to air to regenerate the catalysts under a condition of 550° C. for 5 hours. The temperature was decreased with nitrogen gas purging to a reaction temperature for performing a conversion reaction of toluene and methanol with another ratio and alkylation reaction of ethylene and methanol. Other reaction conditions: in the first reaction zone, the mass hourly space velocity of toluene was 2 h$^{-1}$ and the reaction temperature was 480° C.; in the second reaction zone, the reaction temperature was 400° C. The composition of a mixed product of the first reaction zone and the second reaction zone was analyzed online by using a gas chromatograph respectively. The product distribution was as shown in Table 3 after resultant water was removed, and the product distribution was as shown in Table 4 after the $C_2^-$ component was further removed.

It can be seen from Table 4 that when feed molar ratios of toluene/methanol were 4/1, 2/1, 1/1, and 1/2 respectively, the selectivities of propylene in total products were 24.32 wt %, 27.64 wt %, 33.32 wt %, and 43.12 wt % respectively, and the selectivities of p-xylene were 67.18 wt %, 64.26 wt %, 58.51 wt %, and 47.35 wt % respectively; and the overall selectivities of propylene and p-xylene were 91.50 wt %, 91.90 wt %, 91.83 wt %, and 90.47 wt % respectively. The selectivities of p-xylene in xylene isomers were 99.31 wt %, 99.26 wt %, 99.21 wt %, and 99.14 wt % respectively.

TABLE 3

| | Catalyst TMPC-06 | | | |
|---|---|---|---|---|
| Feeding time (hour) | 1 | 1 | 1 | 1 |
| Toluene/methanol (molar ratio) in the first reaction zone | 4/1 | 2/1 | 1/1 | 1/2 |
| Ethylene/methanol (molar ratio) in the second reaction zone | 1/1 | 1/1 | 1/1 | 1/1 |
| Selectivity of p-xylene in xylene isomers (wt %) | 99.31 | 99.26 | 99.21 | 99.14 |
| Product distribution (wt %) | | | | |
| $CH_4$ | 1.44 | 0.81 | 0.98 | 1.17 |
| $C_2H_4$ | 10.66 | 12.54 | 15.68 | 20.89 |
| $C_2H_6$ | 0.07 | 0.09 | 0.11 | 0.11 |
| $C_3H_6$ | 21.36 | 23.93 | 27.73 | 33.56 |
| $C_3H_8$ | 0.11 | 0.12 | 0.15 | 0.18 |
| $C_4$ | 1.22 | 1.44 | 1.94 | 2.67 |
| $C_5$ | 0.49 | 0.57 | 0.70 | 0.88 |
| Benzene | 0.14 | 0.06 | 0.03 | 0.10 |
| Ethylbenzene | 0.13 | 0.11 | 0.10 | 0.09 |
| p-Xylene | 59.00 | 55.62 | 48.70 | 36.85 |
| m-Xylene | 0.03 | 0.04 | 0.04 | 0.04 |
| o-Xylene | 0.38 | 0.38 | 0.35 | 0.28 |
| $\geq C_9$ | 4.97 | 4.29 | 3.48 | 3.18 |
| Total | 100.00 | 100.00 | 100.00 | 100.00 |

TABLE 4

| | Catalyst TMPC-06 | | | |
|---|---|---|---|---|
| Feeding time (hour) | 1 | 1 | 1 | 1 |
| Toluene/methanol (molar ratio) in the first reaction zone | 4/1 | 2/1 | 1/1 | 1/2 |
| Ethylene/methanol (molar ratio) in the second reaction zone | 1/1 | 1/1 | 1/1 | 1/1 |
| Selectivity of propylene + p-xylene (wt %) | 91.50 | 91.90 | 91.83 | 90.47 |
| Selectivity of p-xylene in xylene isomers (wt %) | 99.31 | 99.09 | 99.21 | 99.14 |
| Product distribution (wt %) | | | | |
| $C_3H_6$ | 24.32 | 27.64 | 33.32 | 43.12 |
| $C_3H_8$ | 0.12 | 0.13 | 0.18 | 0.23 |
| $C_4$ | 1.39 | 1.66 | 2.33 | 3.43 |
| $C_5$ | 0.56 | 0.66 | 0.84 | 1.12 |
| Benzene | 0.16 | 0.07 | 0.04 | 0.13 |
| Ethylbenzene | 0.14 | 0.13 | 0.12 | 0.11 |
| p-Xylene | 67.18 | 64.26 | 58.51 | 47.35 |
| m-Xylene | 0.04 | 0.04 | 0.04 | 0.05 |
| o-Xylene | 0.43 | 0.44 | 0.42 | 0.36 |
| $\geq C_9$ | 5.66 | 4.96 | 4.18 | 4.09 |
| Total | 100.00 | 100.00 | 100.00 | 100.00 |

Comparative Example 1

Preparation of p-Xylene and Co-Production of Ethylene and Propylene Via Reaction of Toluene and Methanol without Further Reaction by Returning $C_2^-$ Component A TMPC-06 catalyst prepared in Example 1 was subjected to tablet compression molding and a 40-60 mesh target catalyst sample was obtained by cracking and sieving. 10 g of the catalyst was charged to a reactor for performing conversion reaction of toluene and methanol. Molar ratios of toluene/methanol were 4/1, 2/1, 1/1, and 1/2 respectively. Once a reaction with a certain ratio therein was completed, nitrogen gas was introduced online for purging and then switched to air to regenerate the catalysts under a condition of 550° C. for 5 hours. The temperature was decreased with nitrogen gas purging to a reaction temperature for performing a conversion reaction of toluene and methanol with another ratio. Other reaction conditions: the mass hourly space velocity of toluene was 2 h$^{-1}$ and the reaction temperature was 480° C. The composition of products was analyzed online by using a gas chromatograph. The product distribution was as shown in Table 5 after resultant water was removed.

When feed molar ratios of toluene/methanol were 4/1, 2/1, 1/1, and 1/2 respectively, the selectivities of propylene in products were 2.93 wt %, 4.66 wt %, 7.89 wt %, and 13.17 wt % respectively.

TABLE 5

| | Catalyst TMPC-06 | | | |
|---|---|---|---|---|
| Feeding time (hour) | 1 | 1 | 1 | 1 |
| Toluene/methanol (molar ratio) in the first reactor | 4/1 | 2/1 | 1/1 | 1/2 |
| Conversion rate of methanol (%) | 100 | 100 | 94.36 | 90.23 |
| Conversion rate of methanol toluene (%) | 14.04 | 23.47 | 31.74 | 36.21 |
| Selectivity of p-xylene in xylene isomers (wt %) | 99.35 | 99.46 | 99.23 | 99.16 |
| Product distribution (wt %) | | | | |
| $CH_4$ | 0.11 | 0.18 | 0.30 | 0.49 |
| $C_2H_4$ | 4.92 | 6.58 | 10.34 | 17.52 |
| $C_2H_6$ | 0.01 | 0.01 | 0.02 | 0.02 |
| $C_3H_6$ | 2.93 | 4.66 | 7.89 | 13.17 |
| $C_3H_8$ | 0.04 | 0.07 | 0.11 | 0.15 |
| $C_4$ | 0.39 | 0.65 | 1.07 | 2.06 |
| $C_5$ | 0.25 | 0.27 | 0.43 | 0.64 |
| Benzene | 0.19 | 0.09 | 0.04 | 0.15 |
| Ethylbenzene | 0.17 | 0.16 | 0.14 | 0.13 |
| p-Xylene | 83.54 | 81.21 | 73.92 | 60.13 |
| m-Xylene | 0.02 | 0.02 | 0.05 | 0.06 |
| o-Xylene | 0.52 | 0.42 | 0.52 | 0.45 |
| $\geq C_9$ | 6.91 | 5.69 | 5.16 | 5.03 |
| Total | 100.00 | 100.00 | 100.00 | 100.00 |

This invention has been described in detail above, but this invention is not limited to specific embodiments described herein. It will be understood by the person skilled in the art that other modifications and variations can be made without departing from the scope of the invention. The scope of the invention is defined by the appended claims.

What is claimed is:

1. A method for preparing p-xylene and co-producing propylene with a high selectivity, comprising the steps of:
    a) continuously bringing a raw material comprising toluene and at least one of methanol and dimethyl ether into contact with a catalyst in a reaction system to obtain a resultant;
    b) separating the resultant into a $C_6+$ component, a $C_4$-$C_5$ component, a $C_3$ component, and an ethylene-enriched $C_2$— component respectively;
    c) returning the ethylene-enriched $C_2$— component to the reaction system to react the ethylene-enriched $C_2$ component with the raw material on the catalyst to produce propylene;
    d) separating p-xylene from the $C_6+$ component; and
    e) separating propylene from the $C_3$ component,
    wherein the catalyst comprises a ZSM-5 and/or ZSM-11 molecular sieve that is hydrothermally treated under an atmosphere of saturated steam at 500-700° C. for 3-6 hours and further subjected to a surface modification by contact with a siloxanyl compound having a formula as shown below:

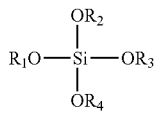

wherein $R_1$, $R_2$, $R_3$, and $R_4$ are each independently a $C_{1-10}$ alkyl group.

2. The method according to claim 1, wherein the reaction system comprises a reactor or a plurality of reactors connected in series and/or in parallel.

3. The method according to claim 2, wherein the reactor is one or more selected from a fixed bed reactor, a fluidized bed reactor, and a moving bed reactor.

4. The method according to claim 1, wherein 1-10 wt % Si is loaded on the catalyst during the surface modification.

5. A method for preparing p-xylene and co-producing propylene with a high selectivity in a reaction system, wherein the reaction system comprises a first reaction zone and a second reaction zone, and the method comprises the steps of:
    a) continuously bringing a raw material comprising toluene and at least one of methanol and dimethyl ether into contact with a catalyst I in the first reaction zone, and then into contact with a catalyst II in the second reaction zone to obtain a resultant;
    b) separating the resultant into a $C_6+$ component, a $C_4$-$C_5$ component, a $C_3$ component, and an ethylene-enriched $C_2$— component respectively;
    c) returning the ethylene-enriched $C_2$— component to the second reaction zone, and reacting the ethylene-enriched $C_2$— component with methanol and/or dimethyl ether in the raw material within the second reaction zone on the catalyst II to produce propylene;
    d) separating p-xylene from the $C_6+$ component; and
    e) separating propylene from the $C_3$ component,
    wherein each of the catalyst I and the catalyst II independently comprises a ZSM-5 and/or ZSM-11 molecular sieve that is hydrothermally treated under an atmosphere of saturated steam at 500-700° C. for 3-6 hours and further subjected to a surface modification by contact with a siloxanyl compound having a formula as shown below:

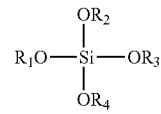

wherein $R_1$, $R_2$, $R_3$, and $R_4$ are each independently a $C_{1-10}$ alkyl group.

6. The method according to claim 5, wherein the first reaction zone and the second reaction zone are in the same reactor.

7. The method according to claim 5, wherein the first reaction zone comprises a reactor or a plurality of reactors connected in series and/or in parallel; the second reaction zone comprises a reactor or a plurality of reactors connected in series and/or in parallel; and the first reaction zone and the second reaction zone are connected in series.

8. The method according to claim 5, wherein 1-10 wt % Si is loaded on the catalyst I and on catalyst II during the surface modification.

9. A method for preparing p-xylene and co-producing propylene with a high selectivity in a reaction system, wherein the reaction system comprises a first reaction zone and a second reaction zone, and the method comprises the steps of:
    a) bringing toluene and a first portion of methanol and/or dimethyl ether into contact with a catalyst I in the first reaction zone to obtain a resultant A;
    b) separating the resultant A into a $C_6+$ component, a $C_4$-$C_5$ component, a $C_3$ component, and an ethylene-enriched $C_2$— component respectively from a separation system;
    c) bringing the ethylene-enriched $C_2$— component and a second portion of methanol and/or dimethyl ether into contact with a catalyst II in the second reaction zone to obtain a resultant B comprising propylene, and feeding the resultant B into the separation system;
    d) separating a p-xylene from the $C_6+$ component; and
    e) separating propylene from the $C_3$ component,
    wherein each of the catalyst I and the catalyst II independently comprises a ZSM-5 and/or ZSM-11 molecular sieve that is hydrothermally treated under an atmosphere of saturated steam at 500-700° C. for 3-6 hours and further subjected to a surface modification by contact with a siloxanyl compound having a formula as shown below:

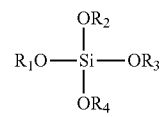

wherein $R_1$, $R_2$, $R_3$, and $R_4$ are each independently a $C_{1-10}$ alkyl group.

10. The method according to claim 9, wherein the first reaction zone comprises a reactor or a plurality of reactors connected in series and/or in parallel; the second reaction zone comprises a reactor or a plurality of reactors connected in series and/or in parallel; and the first reaction zone and the second reaction zone are connected in parallel.

11. The method according to claim 5, wherein 1-10 wt % Si is loaded on the catalyst I and on catalyst II during the surface modification.

* * * * *